United States Patent

Fringeli

Patent Number: 5,423,905
Date of Patent: Jun. 13, 1995

[54] MOTH- AND BEETLE-PROOFING FORMULATION

[75] Inventor: Werner Fringeli, Laufen, Switzerland

[73] Assignee: Ciba-Geigy Corporation, Ardsley, N.Y.

[21] Appl. No.: 276,282

[22] Filed: Jul. 18, 1994

[30] Foreign Application Priority Data

Jan. 27, 1994 [CH] Switzerland ............... 250/94

[51] Int. Cl.$^6$ ............ A01N 47/28; C09D 5/00
[52] U.S. Cl. ............... 106/18.32; 106/18.33; 427/394; 514/594; 514/598; 514/724; 564/47; 564/53; 564/55
[58] Field of Search ............ 106/18.32, 18.33; 514/598, 595, 724; 564/47, 53, 55; 427/394

[56] References Cited

U.S. PATENT DOCUMENTS 2,745,874  5/1956  Schetty et al. .......... 564/53
5,057,539  10/1991  Neukom et al. .......... 514/531

FOREIGN PATENT DOCUMENTS 92-1092  9/1992  South Africa .
0536011  6/1939  United Kingdom .

*Primary Examiner*—Anthony Green
*Attorney, Agent, or Firm*—Kevin T. Mansfield

[57] ABSTRACT

The invention relates to a formulation for protecting keratinous material from attack by pests that feed on keratin, comprising (A) at least one diphenylurea of formula

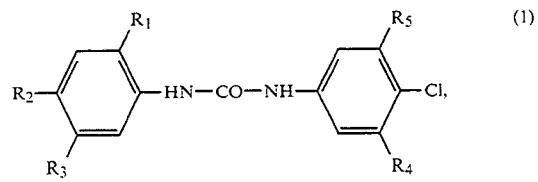

wherein
$R_1$ is hydrogen or 4-chlorophenoxy-6-sulfonate,
$R_2$ is hydrogen or chloro,
$R_3$ is chloro or trifluoromethyl,
$R_4$ is hydrogen or chloro, and
$R_5$ is hydrogen or trifluoromethyl, and
(B) at least one glycol, and to a process for protecting keratinous material against attack by pests that feed on keratin with the novel formulation.

11 Claims, No Drawings

MOTH- AND BEETLE-PROOFING FORMULATION

The present invention relates to a formulation for protecting keratinous material, in particular wool, furs and feathers, against attack by pests that feed on keratin, especially moth and beetle larvae, and to a process for protecting keratinous material from attack by pests that feed on keratin, which comprises treating the material to be protected with the novel composition.

It is known that halogenated and also sulfonated derivatives of diphenylurea act against larvae of the clothes moth, fur moth and carpet beetle. They are therefore suitable for protecting wool, furs and feathers.

The active substance formulations that have so far become known from the prior art are unable to fulfill all current requirements with respect to solubility and ease of handling while having a broad activity spectrum.

The present invention therefore has for its object to provide an active substance formulation that meets current needs.

Surprisingly, an active substance formulation has now been found that meets these requirements.

Accordingly, the invention relates to a formulation for protecting keratinous material from attack by pests that feed on keratin, comprising (A) at least one diphenylurea of formula

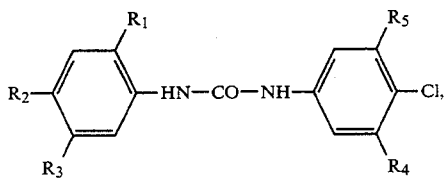

wherein
$R_1$ is hydrogen or 4-chlorophenoxy-6-sulfonate,
$R_2$ is hydrogen or chloro,
$R_3$ is chloro or trifluoromethyl,
$R_4$ is hydrogen or chloro, and
$R_5$ is hydrogen or trifluoromethyl, and
(B) at least one glycol.

The novel formulations preferably comprise as diphenylurea of formula (1) a diphenylurea of formula

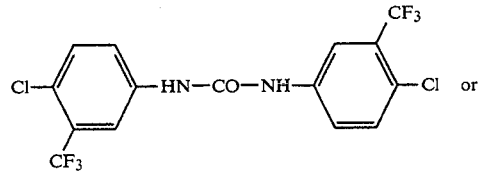

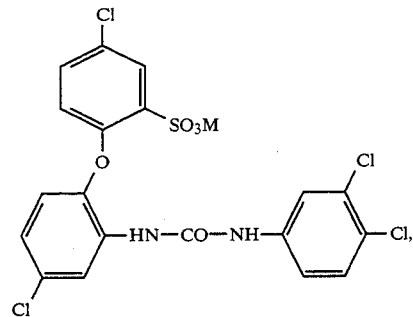

wherein M is an alkali metal cation, preferably sodium.

An alkali metal cation may suitably be sodium, potassium or lithium.

Compound (B) of the novel formulations is preferably propylene glycol, most preferably 1,2-propylene glycol.

A particularly preferred formulation comprises (A) at least one diphenylurea of formula (1), preferably a diphenylurea of formula (3), and (B) at least one glycol, preferably 1,2-propylene glycol.

The novel formulation comprising the compound of formula (3) as diphenylurea and 1,2-propylene glycol as compound (B) is very particularly preferred.

The novel formulations may consist solely of components (A) and (B) or they may comprise other compounds that are effective protective agents against insects that feed on keratin, typically including benzimidazoles, aromatic sulfonamides and phosphates and phosphonates. The formulations may additionally comprise further auxiliaries selected from further solvents, acids, bases, surfactants, wetting agents and dispersants and-/or emulsifiers.

The mixture ratio of the two components (A) and (B) can vary over a wide range. For example, the components (A) and (B) may be in the ratio from 1:3 to 3:1, preferably from 1:2 to 2:1. The most preferred weight ratio of components (A) to (B) is from 1:1 to 1:2.

The compounds of formulae (1), (2) and (3) are known or they can be prepared by methods analogous to known ones.

The novel formulations can be used for protecting keratinous material against insects that feed on keratin, typically against Tineola spec. and Tinea spec., as well as against larvae of Coleoptera that feed on keratin, for example Anthrenus spec. and Attagenus spec. The formulations are admirably suitable for proofing keratinous material against feeding damage by insects, especially for providing such material with a washfast and lightfast finish against insects, in particular against moths and beetles. The keratinous material may be in the untreated as well as in the processed state, for example raw or processed sheep's wool, products made of other animal hairs, hides, furs and feathers.

The preferred utility of the novel formulations is, on the one hand, for protecting woollen textiles such as woollen blankets, wool carpets, woollen underwear, woollen clothing and knitted goods or wool-containing textiles such as blends of which wool is one component, typically blends of wool and other natural fibres, preferably cotton, or blends of wool and man-made fibres, and, on the other hand, also for protecting furs and hides from attack by said pests.

The invention also relates to a process for protecting keratinous material, especially wool textiles, from attack by pests that feed on keratin, typically including: moth and beetle larvae, which process comprises treating the material to be protected with a formulation comprising (A) at least one diphenylurea of formula

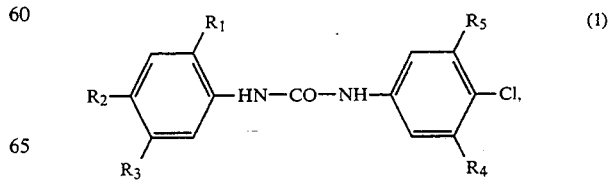

wherein $R_1$ is hydrogen or 4-chlorophenoxy-6-sulfonate,
$R_2$ is hydrogen or chloro,
$R_3$ is chloro or trifluoromethyl,
$R_4$ is hydrogen or chloro, and
$R_5$ is hydrogen or trifluoromethyl, and (B) at least one glycol. To this end, the novel formulation is usually added to a treatment liquor, together with other optional protective agents or auxiliaries, which liquor may additionally contain customary textile auxiliaries and/or dyes, and impregnating the material to be treated with said liquor.

The materials to be protected, preferably textile materials, may be impregnated with hot or cold aqueous dye, bleaching, chroming or aftertreatment baths that contain a specific concentration of novel formulation, by means of different suitable textile finishing methods such as padding or exhaust methods.

The amount of novel formulation added to the treatment bath will depend on the substrate and on the method of application. This amount will, however, usually be such that, after exhaustion on to the material to be protected, said material contains 1.0 to 2000 ppm, preferably 100 to 1000 ppm, of active substance. In the exhaust process at a liquor to goods ratio of 1:20, this amount corresponds to a concentration of 0.001 to 1 g of active substance/liter of treatment bath, depending on the degree of exhaustion achieved. In the pad process, concentrations of up to 2 g of active substance per liter are possible.

With respect to the process for the protection of keratinous material, the same preferred meanings apply as cited in connection with the novel formulations.

Unless otherwise indicated, parts and percentages in the following Examples are by weight.

EXAMPLE 1

132 parts of 1,2-propylene glycol are charged to a 500 ml glass beaker. Then 68 parts of the compound of formula

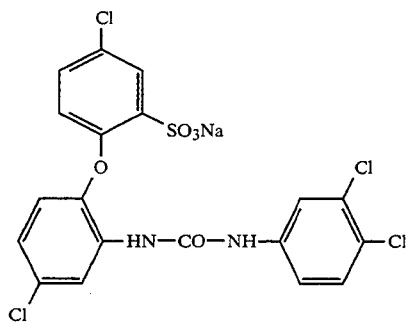

(101)

are added dry. With constant stirring, the mixture is then warmed to 50° C. After about 30 minutes, the solution is allowed to cool, with stirring, to room temperature. The solution is afterwards clarified by filtration. The resultant solution is storage-stable over a period of several months and is admirably suited for use as preservative for protecting animal fibres against feeding damage caused by larvae of the clothes moth, fur moth and carpet beetle.

EXAMPLE 2

Woollen yarn is put at 40° C. and a liquor ratio of 1:10 into a treatment bath comprising, per liter of water, 10 g of sodium sulfate,
3 g of acetic acid and
1 g of the formulation described in Example 1.

The bath is then heated to 100° C. and treatment is carded out in conventional manner. The woollen yarn has good protection against feeding damage by moth and beetle larvae. This protection is retained even after repeated washing of the wool.

EXAMPLE 3

A yarn blend consisting of 80 % of wool and 20 % of polyamide is put at 40° C. and a liquor ratio of 1:10 into a treatment bath comprising, per liter of water, 3 g of ammonium sulfate,
1 g of acetic acid,
1.5 g of a condensate of phenolsulfonic acid, di(hydroxyphenyl)sulfone and formaldehyde,
2 g of a condensate of naphthalenesulfonic acid and formaldehyde and 1 g of the solution described in Example 1.

The bath is then heated to 100° C. and treatment is carried out in conventional manner. The wool component of the treated yarn blend has good protection against feeding damage by moth and beetle larvae. This protection is retained even after repeated washing of the wool.

EXAMPLE 4

A yarn blend consisting of 45 % of wool and 55 % of polyester is put at 40° C. and a liquor ratio of 1:10 into a treatment bath comprising, per liter of water, 1 g of acetic acid,
2 g of a condensate of naphthalensulfonic acid and formaldehyde
3 g of a mixture of methyl cresotinate and a polyadduct of 30 mol of ethylene oxide with castor oil and
0.5 g of the solution described in Example 1.

The bath is then heated to 100° C. and treatment is carried out in conventional manner. The wool component of the treated yarn blend has good protection against feeding damage by moth and beetle larvae. This protection is retained even after repeated washing of the wool.

EXAMPLE 5

Raw wool is washed by the continuous process in a leviathan washer and provided with a moth-and beetle-proof finish. This is done by adjusting the pH of the liquor to below 7 with acetic acid in the last compartment of the leviathan washer and also adding 1 g/liter of water of the solution described in Example 1. Treatment is carded out at 40–60° C. To maintain the concentration in the treatment bath, a further addition of 10 g of the solution described in Example 1 is made per kg of the untreated wool. This further addition is made continuously to the bath in the form of an aqueous solution over the entire treatment time. The treated raw wool has good protection against feeding damage by moths and beetles. The wool can be used for all further treatment processes commonly employed in the textile industry without impairment of its technological properties.

What is claimed is:

1. A formulation for protecting keratinous material from attack by pests that feed on keratin, consisting essentially of (A) at least one diphenylurea of the formula

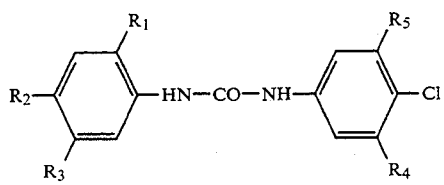

(1)

wherein $R_1$ is hydrogen or 4-chlorophenoxy-6-sulfonate, $R_2$ is hydrogen or chloro, $R_3$ is chloro or trifluoromethyl, $R_4$ is hydrogen or chloro, and $R_5$ is hydrogen or trifluoromethyl, and (B) at least one glycol, wherein the weight ratio of components (A) and (B) is 1:3 to 3:1.

2. A formulation according to claim 1, wherein component (A) is the diphenylurea of formula

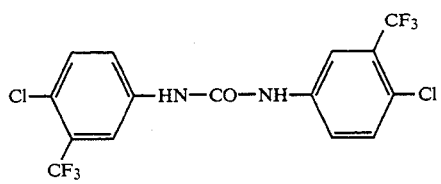

(2)

3. A formulation according to claim 1, wherein component (A) is the diphenylurea of formula

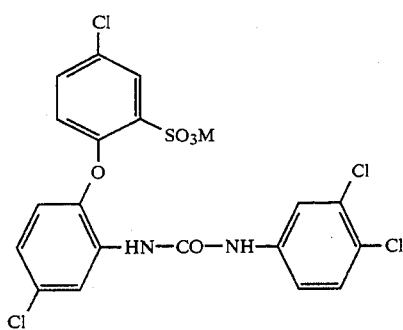

(3)

wherein M is an alkali metal cation.

4. A formulation according to claim 1, wherein component (B) is a propylene glycol.

5. A formulation according to claim 4, wherein component (B) is 1,2-propylene glycol.

6. A formulation according to claim 1, wherein the weight ratio of components (A) to (B) is from 1:1 to 1:2.

7. A process for protecting keratinous material from attack by pests that feed on keratin, which comprises treating the material to be protected with a formulation consisting essentially of (A) at least one diphenylurea of the formula

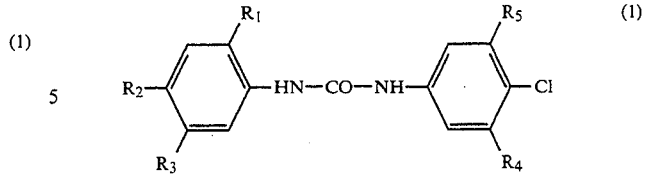

(1)

wherein $R_1$ is hydrogen or 4-chlorophenoxy-6-sulfonate, $R_2$ is hydrogen or chloro, $R_3$ is chloro or trifluoromethyl, $R_4$ is hydrogen or chloro, and $R_5$ is hydrogen or trifluoromethyl, and (B) at least one glycol, wherein the weight ratio of components (A) and (B) is 1:3 to 3:1.

8. A process according to claim 7, wherein the material is treated with a formulation comprising the diphenylurea of formula

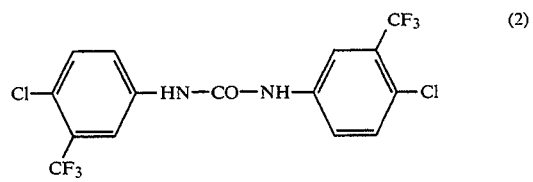

(2)

as component (A).

9. A process according to claim 7, wherein the material is treated with a formulation comprising the diphenyl urea of formula

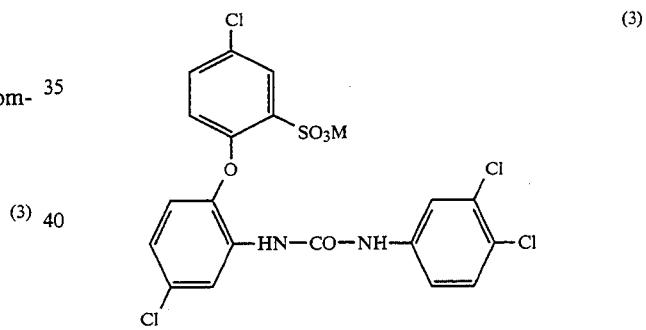

(3)

wherein M is an alkali metal cation, as component (A).

10. A process according to claim 7, wherein the material is treated with a formulation comprising the diphenylurea of formula

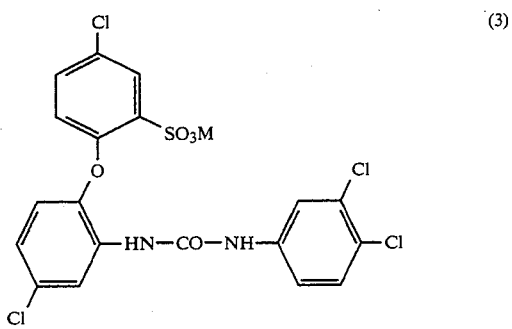

(3)

wherein M is an alkali metal cation as component (A), and 1,2-propylene glycol as component (B).

11. A process according to claim 7, which comprises applying the formulation in a concentration of 10 to 2000 ppm based on the material to be protected, to said material.

* * * * *